US009795317B2

(12) United States Patent
Ochi et al.

(10) Patent No.: US 9,795,317 B2
(45) Date of Patent: Oct. 24, 2017

(54) BODY COMPOSITION MEASUREMENT DEVICE, BODY COMPOSITION MEASUREMENT METHOD, AND CORRECTION METHOD IN BODY COMPOSITION MEASUREMENT

(71) Applicant: Panasonic Intellectual Property Management Co., Ltd., Osaka (JP)

(72) Inventors: Kazuhiro Ochi, Kyoto (JP); Hiroaki Fukuda, Tochigi-ken (JP); Tatsuya Takahashi, Shiga-ken (JP); Jakusei Kiyosaki, Hyogo-ken (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 286 days.

(21) Appl. No.: 14/418,857

(22) PCT Filed: Oct. 23, 2013

(86) PCT No.: PCT/JP2013/006263
§ 371 (c)(1),
(2) Date: Jan. 30, 2015

(87) PCT Pub. No.: WO2014/087570
PCT Pub. Date: Jun. 12, 2014

(65) Prior Publication Data
US 2015/0150478 A1 Jun. 4, 2015

(30) Foreign Application Priority Data
Dec. 5, 2012 (JP) ................ 2012-266522

(51) Int. Cl.
*A61B 5/05* (2006.01)
*A61B 5/053* (2006.01)
*A61B 5/00* (2006.01)

(52) U.S. Cl.
CPC .......... *A61B 5/0537* (2013.01); *A61B 5/0531* (2013.01); *A61B 5/4872* (2013.01);
(Continued)

(58) Field of Classification Search
CPC ...... A61B 5/0537; A61B 5/053; A61B 5/4872
(Continued)

(56) References Cited

U.S. PATENT DOCUMENTS

| 5,611,351 A | 3/1997 | Sato et al. |
| 2005/0203435 A1 | 9/2005 | Nakada |
| 2012/0172747 A1* | 7/2012 | Fukuda ............... A61B 5/0537 600/547 |

FOREIGN PATENT DOCUMENTS

| EP | 1 512 371 A1 | 3/2005 |
| JP | 07-171120 A | 7/1995 |

(Continued)

OTHER PUBLICATIONS

Extended European Search Report issued in Application No. 13859832.1 dated Nov. 23, 2015.
(Continued)

*Primary Examiner* — Daniel Cerioni
(74) *Attorney, Agent, or Firm* — McDermott Will & Emery LLP

(57) ABSTRACT

Provided is a body composition measurement device capable of accurately acquiring visceral fat quantity-related information as body composition-related information of a human body. A body composition measurement device has a voltage detection unit that detects a voltage that occurs at a human-body-mimic resistor in order to measure a resistance value of a compensating resistor unit and detects a voltage that occurs at voltage measurement electrode pair as a result of current that is generated by a current generation unit and that is supplied to the abdomen of the subject via the
(Continued)

current supply electrode pair, and a calculation unit that generates body composition-related information for the subject on the basis of the voltage occurring at the voltage measurement electrode pair and the voltage generated at the human-body-mimic resistor, which have been detected by the voltage detection unit.

6 Claims, 8 Drawing Sheets

(52) U.S. Cl.
CPC .......... *A61B 5/6823* (2013.01); *A61B 5/7278* (2013.01); *A61B 5/742* (2013.01)
(58) Field of Classification Search
USPC ........................................................ 600/547
See application file for complete search history.

(56) References Cited

FOREIGN PATENT DOCUMENTS

| | | |
|---|---|---|
| JP | 2000-152919 A | 6/2000 |
| JP | 2004-089719 A | 3/2004 |
| JP | 2007-151619 A | 6/2007 |
| JP | 2011-025071 A | 2/2011 |

OTHER PUBLICATIONS

International Search Report issued in International Application No. PCT/JP2013/006263 dated Dec. 10, 2013.
International Preliminary Report on Patentability dated Jun. 9, 2015 issued in International Patent Application No. PCT/JP2013/006263.

* cited by examiner

BODY COMPOSITION MEASUREMENT DEVICE, BODY COMPOSITION MEASUREMENT METHOD, AND CORRECTION METHOD IN BODY COMPOSITION MEASUREMENT

RELATED APPLICATIONS

This application is the U.S. National Phase under 35 U.S.C. §371 of International Application No. PCT/JP2013/006263, filed on Oct. 23, 2013, which in turn claims the benefit of Japanese Application No. 2012-266522, filed on Dec. 5, 2012, the disclosures of which are incorporated by reference herein.

TECHNICAL FIELD

The present invention relates to a body composition measurement device for measuring the composition of a human body, a body composition measurement method, and a correction method in body composition measurement.

BACKGROUND ART

Visceral fat, which is one of the body compositions that is accumulated in the body, is deeply related to lifestyle related diseases such as diabetes, high blood pressure, and the like. It is thus important to periodically check the amount of visceral fat from the standpoint of health management. The amount of visceral fat can be accurately measured using a cross-sectional image of the abdomen generated by a CT scan. However, the generation of an image with a CT scan involves a large amount of radiation and is thus not suited for a device used to perform frequent measurements. Patent document 1 discloses a technique for measuring the amount of visceral fat through an electrical impedance method.

PRIOR ART DOCUMENT

Patent Document

Patent Document 1: Japanese Laid-Open Patent Publication No. 2007-151619

SUMMARY OF THE INVENTION

Problems that are to be Solved by the Invention

The amount of visceral fat can be estimated from a human body resistance of the abdomen of a measuring subject. A visceral fat amount measurement device measures the human body resistance with a current application electrode pair and a voltage measurement electrode pair arranged around the abdomen of the measuring subject. The visceral fat amount measurement device corrects the amount of visceral fat based on a subcutaneous fat thickness measured with a subcutaneous fat thickness measuring means. The human body resistance at the abdomen of the human body used to measure the amount of visceral fat is a small value of about $0.5\Omega$ to $5\Omega$. Compared to such human body resistance, a contact resistance of the electrode that contacts the abdomen is about $50\Omega$ to $200\Omega$, which is a value of about two digits greater. The contact resistance greatly changes in accordance with the condition in which the current application electrode pair and the voltage measurement electrode pair contact the human body. Thus, in an impedance measurement of the abdomen of the human body, the influence of the contact resistance needs to be reduced to accurately measure the slight resistance. There is room for improvement to reduce measurement errors when measuring the amount of visceral fat using the impedance measurement of the abdomen of the human body.

The present invention has been made on the basis of the background described above, and an object of the present invention is to provide a body composition measurement device that is capable of measuring the amount of visceral fat serving as body composition related information of the human body with high accuracy, a method for measuring body composition, and a method for correcting a body composition measurement.

Means for Solving the Problem (1) A first means includes "a body composition measurement device comprising a current supply electrode pair and a voltage measurement electrode pair that contact a body trunk of a measuring subject; a correction resistor unit; a connection unit connectable to the correction resistor unit; a current generation unit that generates current; a voltage detection unit that detects, through the connection unit, voltage generated by the correction resistor unit to measure resistance of the correction resistor unit, wherein the voltage detection unit detects voltage generated by the voltage measurement electrode pair using current generated by the current generation unit and supplied to the body trunk of the measuring subject through the current supply electrode pair; and a computation unit that generates body composition related information based on the voltage generated by the voltage measurement electrode pair and the voltage generated by the correction resistor unit, which are detected by the voltage detection unit."

The body composition measurement devices includes a current generation unit, a voltage detection unit, a computation unit, a current supply electrode pair, a voltage measurement electrode pair, and a connection unit that can be connected to a correction resistor unit. The connection unit of the body composition measurement device is configured so as to be connectable and separable with respect to the correction resistor unit. According to such configuration, the body composition measurement device can measure the resistance of the correction resistor unit using the circuit block and the measurement path used in the human body resistance measurement of the measuring object by connecting the correction resistor unit to the connection unit. Thus, the body composition measurement device can check the characteristic variation and the characteristic fluctuation of the circuit block and the measurement path used in the human body resistance measurement of the measuring subject. The body composition measurement device thus can reflect the measurement result of the resistance of the correction resistor unit on the body composition measuring method on the body composition measuring method of the measuring subject. Furthermore, the body composition measurement device can measure the amount of visceral fat of the measuring subject with a simple configuration by separating the correction resistor unit from the connection unit. Moreover, the body composition measurement device can estimate, with high accuracy, the measurement of the amount of visceral fat of the measuring subject with a simple configuration using the body composition measuring method on which the measurement result of the resistance of the correction resistor unit is reflected.

(2) A second means includes "a body composition measurement device comprising a current supply electrode pair and a voltage measurement electrode pair that contact a body trunk of a measuring subject; a current generation unit that generates current; a voltage detection unit that detects voltage generated by the correction resistor unit to measure resistance of the correction resistor unit, wherein the voltage detection unit detects voltage generated by the voltage measurement electrode pair using current generated by the current generation unit and supplied to the body trunk of the measuring subject through the current supply electrode pair; and a computation unit that generates body composition related information based on the voltage generated by the voltage measurement electrode pair and the voltage generated by the correction resistor unit, which are detected by the voltage detection unit."

(3) A third means includes "the computation unit generates visceral fat amount related information as the body composition related information."

(4) A fourth means includes "the body composition measurement device comprising an operation unit that generates a control signal; and a switching unit that supplies either one of the current supply electrode pair and the correction resistor unit with the current generated by the current generation unit in accordance with the control signal generated by the operation unit, wherein the switching unit selects the voltage of either one of the voltage measurement electrode pair and the correction resistor unit and supplies the voltage to the voltage detection unit in accordance with the control signal.

(5) A fifth means includes "the correction resistor unit includes one or more simulation resistor units, and the one or more simulation resistor units includes a human body simulation resistor that simulates an abdomen of a measuring subject, a first electrode contact simulation resistor and a second electrode contact simulation resistor that simulate contact of the current supply electrode pair and the abdomen of the measuring subject, and a third electrode contact simulation resistor and a fourth electrode contact simulation resistor that simulate contact of the voltage measurement electrode pair and the abdomen of the measuring subject."

(6) A sixth means includes the switching unit includes a first switching circuit and a second switching circuit; the current supply electrode pair includes a first current supply electrode and a second current supply electrode; each of the first switching circuit and the second switching circuit includes a common terminal, into which the current generated by the current generation unit is input, and a first terminal and a second terminal, from which the current generated by the current generation unit is output; the first terminal of the first switching circuit is connected to the first current supply electrode by a first wiring unit; the second terminal of the first switching circuit is connected to the second current supply electrode by a second wiring unit; the first terminal of the second switching circuit is connected to the second current supply electrode by a third wiring unit; the second terminal of the second switching circuit is connected to the first current supply electrode by a fourth wiring unit; the first wiring unit and the fourth wiring unit are arranged to form a substantially symmetrical geometric shape, and the second wiring unit and the third wiring unit are arranged to form a substantially symmetrical geometric shape; and the first switching circuit and the second switching circuit alternately output the current generated by the current generation unit from the first terminal and the second terminal.

(7) A seventh means includes "each of the current supply electrode pair and the voltage measurement electrode pair includes a plurality of disconnected regions that are electrically disconnected; the switching unit supplies one of the plurality of disconnected regions with the current generated by the current generation unit in accordance with the control signal generated by the operation unit; and the switching unit selects a voltage of one of the plurality of disconnected regions and supplies the voltage to the voltage detection unit in accordance with the control signal generated by the operation unit."

(8) An eighth means includes "a method for correcting a body composition measurement of a body composition measurement device including a current supply electrode pair, a voltage measurement electrode pair, a correction resistor unit, and a connection unit, the method comprising the steps of connecting the correction resistor unit to the connection unit, measuring resistance of the correction resistor unit, and reflecting the resistance on the body composition measurement.

(9) A ninth means includes "a body composition measuring method for measuring a body composition with a body composition measurement device including a current supply electrode pair, a voltage measurement electrode pair, and a correction resistor unit, the method comprising the steps of measuring resistance of the correction resistor unit, holding the current supply electrode pair and the voltage measurement electrode pair in contact with an abdomen of a measuring subject to measure voltage of the voltage measurement electrode pair, and generating body composition related information based on the voltage of the voltage measurement electrode pair and the resistance."

(10) A tenth means includes "the step of generating the body composition related information includes generating visceral fat amount related information."

Effect of the Invention

The body composition measurement device, the method for measuring body composition, and the method for correcting a body composition measurement contribute to measuring the amount of visceral fat, which is one of the compositions of the body, with high accuracy.

EMBODIMENTS OF THE INVENTION

First Embodiment

Figure 1:
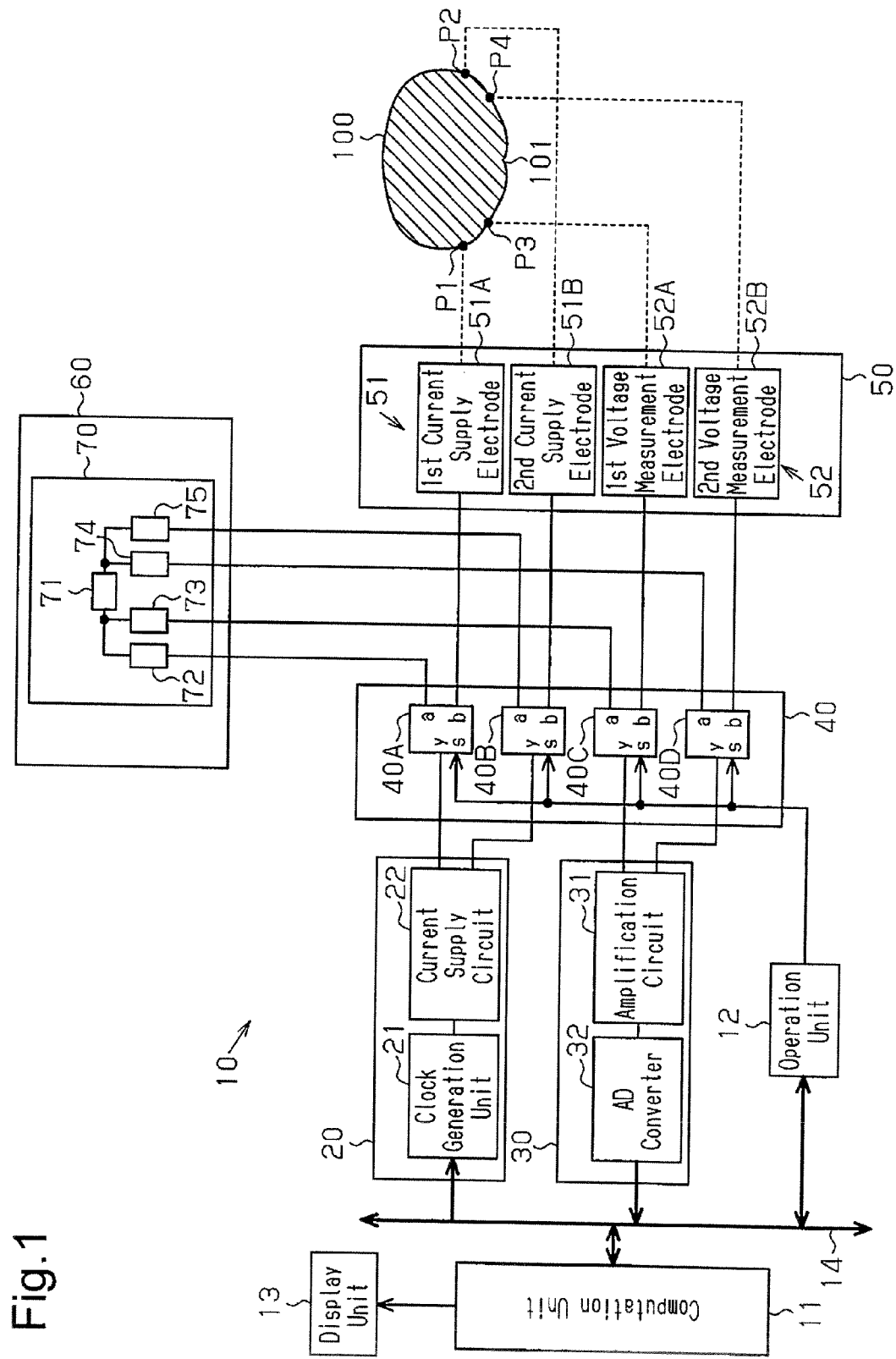
FIG. 1 is a block diagram of a body composition measurement device in a first embodiment.

A body composition measurement device 10 will be described with reference to the block diagram of FIG. 1.

The body composition measurement device 10 for measuring an amount of visceral fat includes a current generation unit 20, a voltage detection unit 30, a computation unit 11, an operation unit 12, a display unit 13, and a bus 14. The current generation unit 20 includes a clock generation circuit 21 and a current supply circuit 22. The voltage detection unit 30 includes an amplification circuit 31 and an AD converter 32. The computation unit 11 is configured by a microcontroller, for example, and has both a computation function and a control function.

The clock generation circuit 21 of the current generation unit 20 generates a clock signal of a predetermined frequency in accordance with a control signal provided from the computation unit 11 via the bus 14. When receiving the clock signal generated by the clock generation circuit 21, the current supply circuit 22 generates an alternating current (AC) to supply to a visceral fat amount measuring portion of a measuring subject. The amplification circuit 31 of the voltage detection unit 30 amplifies a slight voltage measured by the visceral fat amount measuring portion of the measuring subject. The AD converter 32 rectifies and smoothens the output of the amplification circuit 31, and then converts the output to a digital signal. The AD converter 32 provides the digital signal output to the computation unit 11 via the bus 14. The operation unit 12 has a plurality of operation switches that are operated by the measuring subject when performing the measurement of the body composition using the body composition measurement device 10.

The body composition measurement device 10 includes a switching unit 40, an electrode unit 50, and a correction resistor unit 60. The switching unit 40 includes a first switching circuit 40A, a second switching circuit 40B, a third switching circuit 40C, and a fourth switching circuit 40D. The electrode unit 50 includes a current supply electrode pair 51 and a voltage measurement electrode pair 52. The current supply electrode pair 51 includes a first current supply electrode 51A and a second current supply electrode 51B. The voltage measurement electrode pair 52 includes a first voltage measurement electrode 52A and a second voltage measurement electrode 52B. The correction resistor unit 60 includes a simulation resistor unit 70. The simulation resistor unit 70 includes a human body simulation resistor 71, a first electrode contact simulation resistor 72, a second electrode contact simulation resistor 75, a third electrode contact simulation resistor 73, and a fourth electrode contact simulation resistor 74.

The first switching circuit 40A, the second switching circuit 40B, the third switching circuit 40C, and the fourth switching circuit 40D of the switching unit 40 connects a common terminal (y) to either one of a first terminal (a) and a second terminal (b) in accordance with a level of a control signal input to a control terminal (s). The computation unit 11 and the operation unit 12 generate the control signal provide to the control terminals (s) of the first switching circuit 40A, the second switching circuit 40B, the third switching circuit 40C, and the fourth switching circuit 40D. The first switching circuit 40A and the second switching circuit 40B supply the alternating current supplied from the current supply circuit 22 to the current supply electrode pair 51 or one of the first electrode contact simulation resistor 72 and the second electrode contact simulation resistor 75 according to the output signal of the operation unit 12. The third switching circuit 40C and the fourth switching circuit 40D select the voltage of the voltage measurement electrode pair 52 or one of the voltage of the third electrode contact simulation resistor 73 and the fourth electrode contact simulation resistor 74, and inputs the voltage to the amplification circuit 31 of the voltage detection unit 30 according to the output signal of the operation unit 12. That is, the switching unit 40 selects either one of the electrode unit 50 and the correction resistor unit 60 according to the control signal from the computation unit 11 and the operation unit 12.

When measuring the amount of visceral fat of the measuring subject using the body composition measurement device 10, the current supply electrode pair 51 and the voltage measurement electrode pair 52 of the electrode unit 50 are held in contact with a body trunk of the measuring subject. The current supply electrode pair 51 and the voltage measurement electrode pair 52 of the electrode unit 50 are held in contact with areas at positions (P1), (P2), (P3) and (P4) of the outer part, for example, of the abdomen 100 in the body trunk of the measuring subject. FIG. 1 shows a cross-section of the abdomen 100 of the measuring subject, where 101 indicates the umbilicus.

The operation of the body composition measurement device 10 will now be described.

When the switching unit 40 selects the electrode unit 50, the alternating current generated by the current supply circuit 22 is supplied to between the positions (P1) and (P2) of the abdomen 100 of the measuring subject through the first switching circuit 40A, the second switching circuit 40B, and the current supply electrode pair 51. The voltage generated at the positions (P3) and (P4) of the abdomen 100 of the measuring subject is input to the amplification circuit 31 through the voltage measurement electrode pair 52, the third switching circuit 40C, and the fourth switching circuit 40D. The voltage output amplified by the amplification circuit 31 is converted to the digital signal by the AD converter 32, and provided to the computation unit 11. The output of the AD converter 32 corresponds to a value in which the human body resistance between the positions (P1) and (P2) of the abdomen 100 of the measuring subject is obtained through the four-terminal method.

When estimating the amount of visceral fat based on the measured human body resistance between the positions (P1) and (P2) of the abdomen 100 of the measuring subject, the estimation accuracy can be enhanced by taking into consideration the characteristic variation and the characteristic fluctuation of the circuit block and the measurement path used in the measurement.

The body composition measurement device 10 checks the characteristic variation and the characteristic fluctuation by measuring the resistance that serves as a reference with the circuit block and the measurement path used in the measurement. The human body simulation resistor 71 of the simulation resistor unit 70 is a highly accurate resistor having an extremely small temperature dependency and voltage dependency. That is, the resistance of the human body simulation resistor 71 can be used as a reference value.

When the switching unit 40 selects the correction resistor unit 60, the alternating current generated by the current supply circuit 22 is supplied to the human body simulation resistor 71 through the first switching circuit 40A, the second switching circuit 40B, the first electrode contact simulation resistor 72, and the second electrode contact simulation resistor 75. The voltage generated at both ends of the human body simulation resistor 71 is input to the amplification circuit 31 through the third electrode contact simulation resistor 73, the fourth electrode contact simulation resistor 74, the third switching circuit 40C, and the fourth switching circuit 40D. The output of the amplification circuit 31 is converted to a digital signal by the AD converter 32, and provided to the computation unit 11. The computation unit 11 obtains a measurement value of the human body simulation resistor 71 from the value of the input digital signal. That is, the body composition measurement device 10 measures the value of the human body simulation resistor 71 through the four-terminal method. The human body simulation resistor 71 is set to a small value that is about the same as the human body resistance between the positions (P1) and (P2) of the abdomen 100 of the measuring subject. The first electrode contact simulation resistor 72, the second electrode contact simulation resistor 75, the third electrode contact simulation resistor 73, and the fourth electrode contact simulation resistor 74 are set to values of the same extent as the contact resistance of the current supply electrode pair 51 and the voltage measurement electrode pair 52, and the abdomen 100 of the measuring subject.

The computation unit 11 holds resistance information of the human body simulation resistor 71 as a reference value. When estimating the amount of visceral fat of the measuring subject from the voltage output from the AD converter 32 and detected by the voltage detection unit 30 through the voltage measurement electrode pair 52, the computation unit 11 outputs the estimation result reflecting the shift between the measurement value of the human body simulation resistor 71 and the resistance held as the reference value. The computation unit 11 displays the estimation result on the display unit 13.

Figure 2:
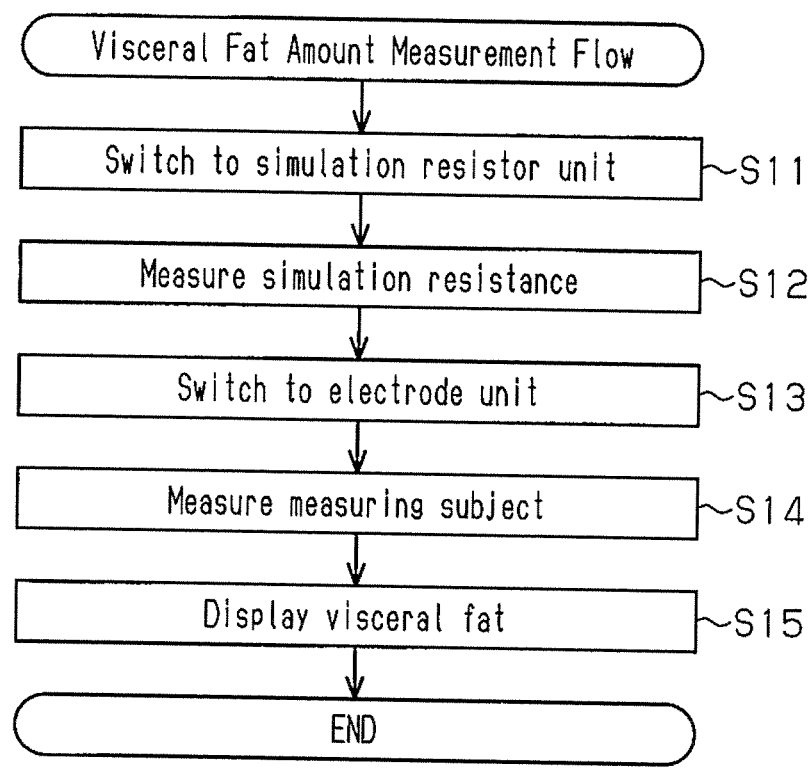
FIG. 2 is a flowchart of a visceral fat amount measurement performed by the body composition measurement device in the first embodiment.

The flow of the measurement of the amount of visceral fat of the measuring subject using the body composition measurement device 10 will now be described with reference to FIG. 2.

The computation unit 11 and the measuring subject sequentially execute steps S11 to S15 when measuring the amount of visceral fat using the body composition measurement device 10.

When measuring the amount of visceral fat, the measuring subject controls the switching unit 40 through the operation of the operation unit 12 in step S11. The switching unit 40 selects the correction resistor unit 60. In step S12, the computation unit 11 measures the resistance of the human body simulation resistor 71 of the simulation resistor unit 70. The computation unit 11 stores the measured resistance. In step S13, the measuring subject controls the switching unit 40 through the operation of the operation unit 12. The switching unit 40 selects the electrode unit 50. In step S14, the voltage detection unit 30 detects the voltage generated by the current supplied to the abdomen 100 of the measuring subject. In step S15, the computation unit 11 estimates the amount of visceral fat based on the output of the AD converter 32 and the measured resistance of the human body simulation resistor 71, and displays the same on the display unit 13.

The body composition measurement device 10 of the present embodiment has the following advantages.

(1) The body composition measurement device 10 includes the computation unit 11, the operation unit 12, the switching unit 40, the electrode unit 50, and the correction resistor unit 60. The switching unit 40 selects either one of the electrode unit 50 and the correction resistor unit 60 based on the control signal from the computation unit 11 and the operation unit 12. The body composition measurement device 10 also includes the current generation unit 20 and the voltage detection unit 30. The correction resistor unit 60 is formed by a highly accurate resistor having an extremely small temperature dependency and voltage dependency. The computation unit 11 estimates the amount of visceral fat based on the voltage generated by supplying current to the abdomen 100 of the measuring subject and the resistance obtained by measuring the human body simulation resistor 71 of the correction resistor unit 60. According to such configuration, the body composition measurement device 10 uses the same circuit block to supply current to and detect voltage at the abdomen 100 of the measuring subject and the correction resistor unit 60. The body composition measurement device 10 checks the difference between the resistance obtained by measuring the correction resistor unit 60 and the resistance serving as the reference value as the characteristic variation and the characteristic fluctuation of the circuit block and the measurement path used in the measurement. Thus, the body composition measurement device 10 estimates the amount of visceral fat with high accuracy taking into consideration the characteristic variation and the characteristic fluctuation of the circuit block and the measurement path used in the measurement.

(2) The body composition measurement device 10 includes the simulation resistor unit 70. The simulation resistor unit 70 includes the human body simulation resistor 71, the first electrode contact simulation resistor 72, the second electrode contact simulation resistor 75, the third electrode contact simulation resistor 73, and the fourth electrode contact simulation resistor 74. The human body simulation resistor 71 is set to a small value that is about the same as the human body resistance between the positions (P1) and (P2) of the abdomen 100 of the measuring subject. The first electrode contact simulation resistor 72, the second electrode contact simulation resistor 75, the third electrode contact simulation resistor 73, and the fourth electrode contact simulation resistor 74 are set to values of the same extent as the contact resistance of the current supply electrode pair 51 and the voltage measurement electrode pair 52 with the abdomen 100 of the measuring subject. According to such configuration, the body composition measurement device 10 performs the measurement with the characteristics of the measurement path of the human body simulation resistor 71, which serves as the reference resistance, brought close to the characteristics of the measurement path of the abdomen 100 of the measuring subject. Thus, the body composition measurement device 10 estimates the visceral fat amount related information with higher accuracy.

Second Embodiment

Compared to the body composition measurement device 10 of the first embodiment, the body composition measurement device 10 of a second embodiment differs in the following portions but is otherwise the same. Same reference numerals are given to those components that are the same as the corresponding components of the first embodiment. Such components will not be described in detail.

In the body composition measurement device 10 of the first embodiment, the correction resistor unit 60 includes the simulation resistor unit 70. In the body composition measurement device 10 of the second embodiment, the correction resistor unit 60 includes at least two or more simulation resistor units.

The configuration of the body composition measurement device 10 of the second embodiment will now be described with reference to the block diagram of FIG. 3.

The body composition measurement device 10 includes the switching unit 40 and the correction resistor unit 60. The switching unit 40 includes a fifth switching circuit 41A, a sixth switching circuit 41B, a seventh switching circuit 41C, and an eighth switching circuit 41D. The correction resistor unit 60 includes a second simulation resistor unit 70A and a third simulation resistor unit 70B serving as the simulation resistor units.

The fifth switching circuit 41A, the sixth switching circuit 41B, the seventh switching circuit 41C, and the eighth switching circuit 41D of the switching unit 40 connect the common terminal (y) to any one of the first terminal (a), the second terminal (b), and a third terminal (c) in accordance with the control signal input to the control terminal (s). That is, the switching unit 40 selects one of the electrode unit 50, the second simulation resistor unit 70A, and the third simulation resistor unit 70B in accordance with a control signal from the computation unit 11 and the operation unit 12.

The second simulation resistor unit 70A includes a second human body simulation resistor 71A, a fifth electrode contact simulation resistor 72A, a sixth electrode contact simulation resistor 75A, a seventh electrode contact simulation resistor 73A, and an eighth electrode contact simulation resistor 74A.

When the switching unit 40 selects the second simulation resistor unit 70A, the alternating current generated by the current supply circuit 22 is supplied to the second human body simulation resistor 71A through the fifth switching circuit 41A, the sixth switching circuit 41B, the fifth electrode contact simulation resistor 72A, and the sixth electrode contact simulation resistor 75A. The voltage generated at both ends of the second human body simulation resistor 71A is input to the amplification circuit 31 through the seventh electrode contact simulation resistor 73A, the eighth electrode contact simulation resistor 74A, the seventh switching circuit 41C, and the eighth switching circuit 41D. The output of the amplification circuit 31 is converted to a digital signal by the AD converter 32 and provided to the computation unit 11. The computation unit 11 obtains the measurement value of the second human body simulation resistor 71A from the value of the input digital signal.

The third simulation resistor unit 70B includes a third human body simulation resistor 71B, a ninth electrode contact simulation resistor 72B, a tenth electrode contact simulation resistor 75B, an eleventh electrode contact simulation resistor 73B, and a twelfth electrode contact simulation resistor 74B. The third human body simulation resistor 71B is set to have a resistance that differs from the second human body simulation resistor 71A.

When the switching unit 40 selects the third simulation resistor unit 70B, the alternating current generated by the current supply circuit 22 is supplied to the third human body simulation resistor 71B through the fifth switching circuit 41A, the sixth switching circuit 41B, the ninth electrode contact simulation resistor 72B, and the tenth electrode contact simulation resistor 75B. The voltage generated at both ends of the third human body simulation resistor 71B is input to the amplification circuit 31 through the eleventh electrode contact simulation resistor 73B, the twelfth electrode contact simulation resistor 74B, the seventh switching circuit 41C, and the eighth switching circuit 41D. The output of the amplification circuit 31 is converted to the digital signal by the AD converter 32 and provided to the computation unit 11. The computation unit 11 obtains the measurement value of the third human body simulation resistor 71B from the value of the input digital signal.

Figure 3:
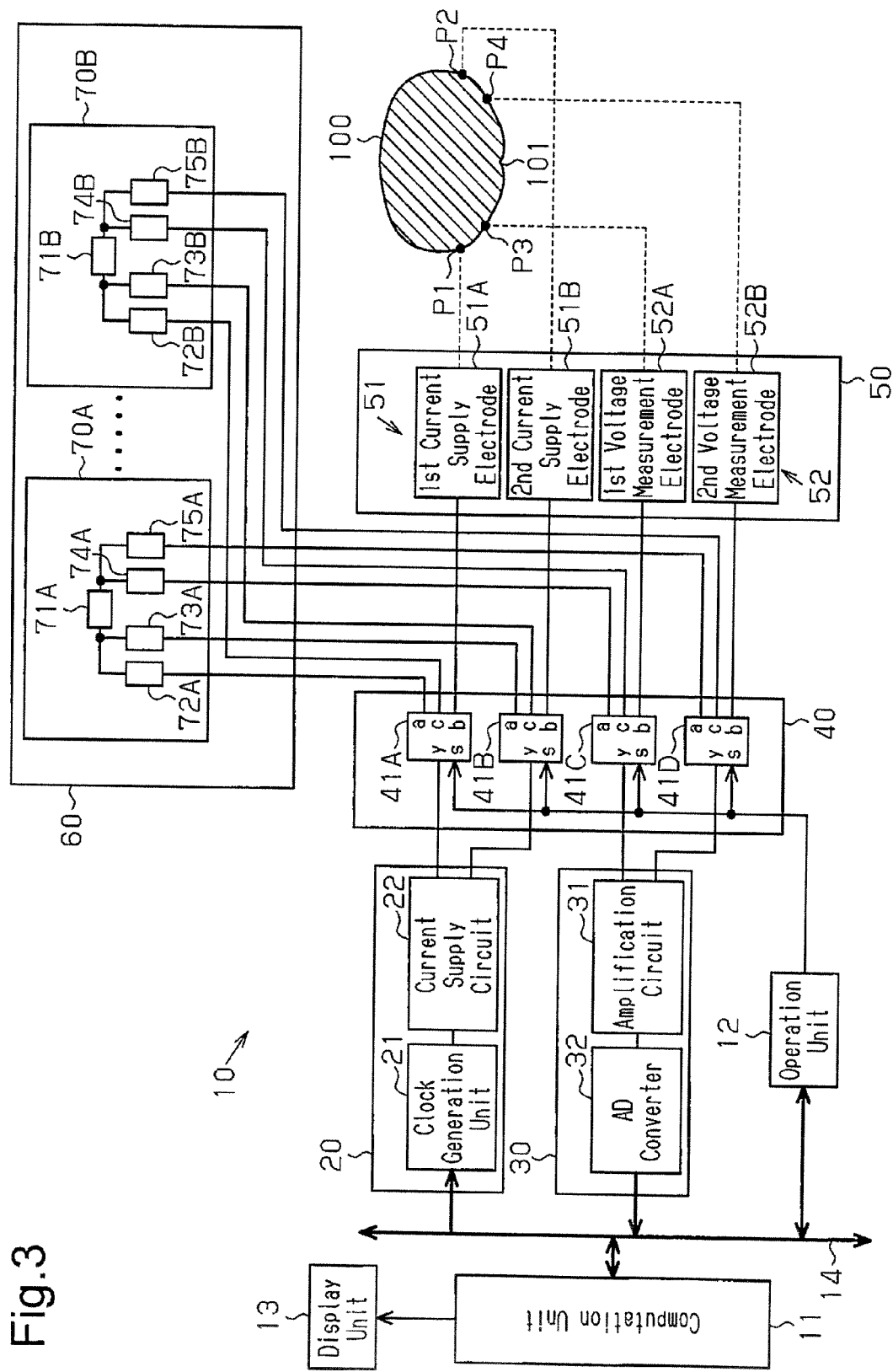
FIG. 3 is a block diagram of a body composition measurement device in a second embodiment.

The configuration of the correction resistor unit 60 is not limited to the example shown in FIG. 3. For example, the correction resistor unit 60 may further include a fourth simulation resistor unit 70C, which has the same circuit configuration as the second simulation resistor unit 70A and the third simulation resistor unit 70B, as the simulation resistor units. A fourth human body simulation resistor 71C of the fourth simulation resistor unit 70C is set to have a resistance that differs from the second human body simulation resistor 71A and the third human body simulation resistor 71B. The switching circuit of the switching unit 40 can select any one of the electrode unit 50, the second simulation resistor unit 70A, the third simulation resistor unit 70B, and the fourth simulation resistor unit 70C according to a control signal from the operation unit 12.

Figure 4:
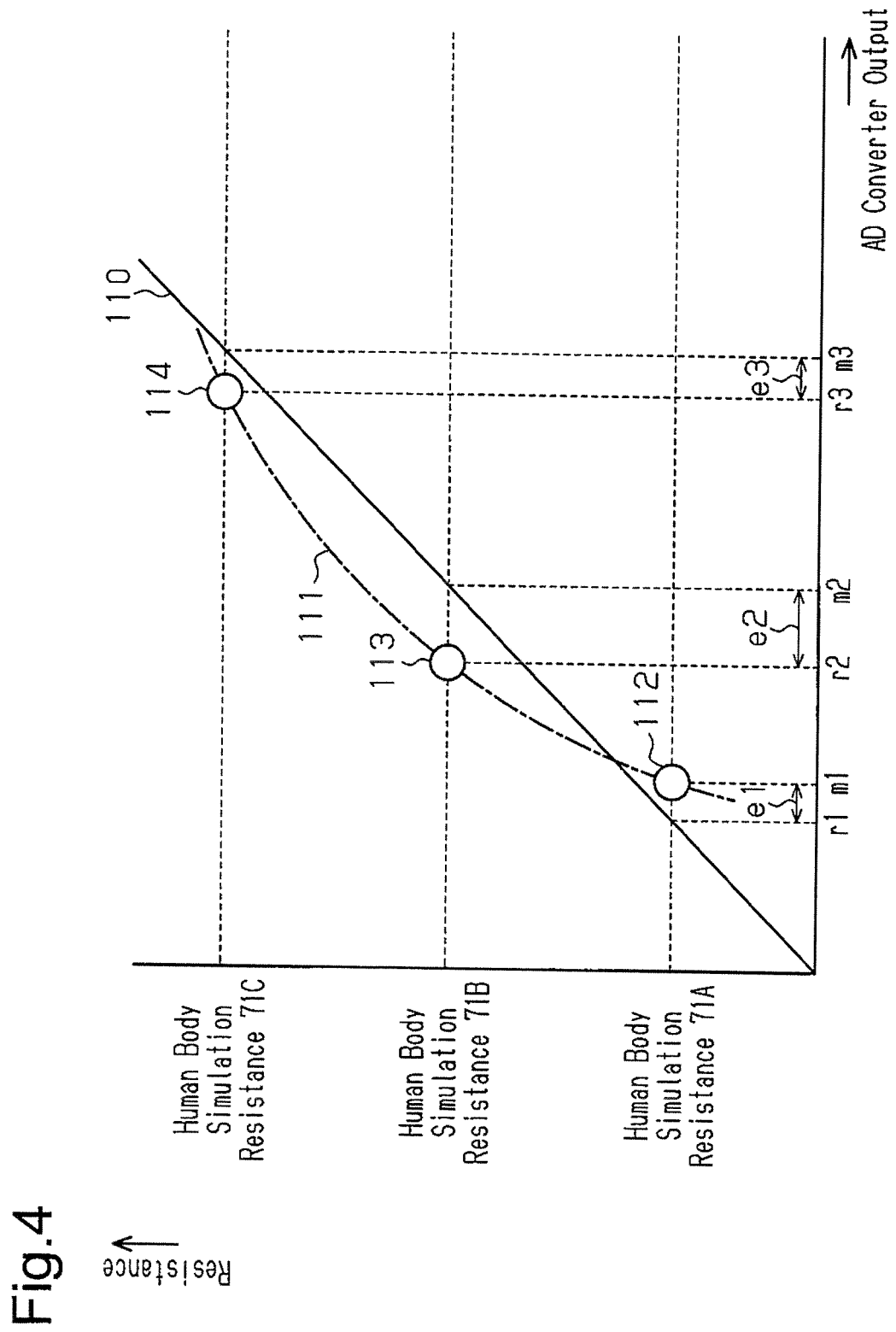
FIG. 4 is a graph of a characteristic variation and a characteristic fluctuation of a measurement circuit block and a measurement path in the body composition measurement device of the second embodiment.

FIG. 4 shows an example of the measurement value of the human body simulation resistor 71 in the second simulation resistor unit 70A, the third simulation resistor unit 70B, and the fourth simulation resistor unit 70C. FIG. 4 shows the relationship of the resistance and an AD converter output value output by the AD converter 32 during measurement by the human body simulation resistor 71. The solid line in FIG. 4 is the ideal line 110 representing the characteristics in the ideal state without the characteristic variation and the characteristic fluctuation in the circuit block and the measurement path used in the measurement. The relationship of the AD converter output value and the resistance is proportional in which the gradient is 45 degrees.

If a characteristic variation and the characteristic fluctuation exist in the circuit block and the measurement path used in the measurement, the measurement value of the human body simulation resistor 71 serving as the reference resistance in the second simulation resistor unit 70A, the third simulation resistor unit 70B, and the fourth simulation resistor unit 70C is shifted from the ideal line 110. A first plotting point 112, a second plotting point 113, and a third plotting point 114 shown in FIG. 4 each show an example of the measurement value of the human body simulation resistor 71 serving as the reference resistance in the second simulation resistor unit 70A, the third simulation resistor unit 70B, and the fourth simulation resistor unit 70C.

In the AD converter output axis, (r1), (r2) and (r3) are shown as the AD converter output values of the human body simulation resistor 71 when the circuit block and the measurement path used in the measurement are in the ideal state. In the AD converter output axis, (m1), (m2), and (m3) show the AD converter output values when the human body simulation resistor 71 is measured with the circuit block and the measurement path, which are used in the measurement. In the AD converter output axis, (e1), (e2), and (e3), which are the differences of (r1), (r2), and (r3) from (m1), (m2), and (m3), are measurement errors caused by the characteristic variation and the characteristic fluctuation of the circuit block and the measurement path, which are used in the measurement.

The broken line (111) shown in FIG. 4 is an approximate curve derived from the measurement value of the human body simulation resistor 71 in the computation unit 11. The approximate curve 111 can be derived, for example, with a least square method. FIG. 4 shows a case in which there are three types of resistance at the human body simulation resistor 71, in which a more accurate curve can be derived when there are more values of the human body simulation resistor 71.

The body composition measurement device 10 takes into consideration the difference of the ideal line 110 and the approximate curve 111 when estimating the amount of visceral fat based on the measured human body resistance between the positions (P1) and (P2) of the abdomen 100 of the measuring subject. That is, the body composition measurement device 10 obtains the resistance using the approximate curve 111 from the AD converter output value output by the AD converter 32 during measurement of the human body resistance of the measuring subject and estimates the amount of visceral fat based on the resistance.

The body composition measurement device 10 of the present embodiment has advantages (1) and (2) of the body composition measurement device 10 of the first embodiment. That is, effect of being able to estimate the amount of visceral fat with high accuracy is obtained. The body composition measurement device 10 of the present embodiment also has the following advantage.

(3) In the body composition measurement device 10, the correction resistor unit 60 includes at least two or more simulation resistor units. The body composition measurement device 10 includes the switching unit 40 for selecting one of the simulation resistor units and the electrode unit 50 in accordance with the control signal from the operation unit 12. According to such configuration, the computation unit 11 can derive the approximate curve using the measurement values of the plurality of human body simulation resistors 71 serving as the reference resistance of the plurality of simulation resistor units. Thus, the body composition measurement device 10 determines the characteristic variation and the characteristic fluctuation of the circuit block and the measurement path used in the measurement with high accuracy. When estimating the amount of visceral fat of the measuring subject, the body composition measurement device 10 generates outputs in view of the characteristic variation and the characteristic fluctuation using the approximate curve. Thus, the body composition measurement device 10 estimates the amount of visceral fat with high accuracy even if the characteristic variation amount and the characteristic fluctuation amount of the circuit block and the measurement path used in the measurement differ depending on the value of the human body resistance of the measuring subject.

Third Embodiment

Compared to the body composition measurement device 10 of the second embodiment, the body composition measurement device 10 of a third embodiment differs in the following portions but is otherwise the same. Same reference numerals are given to those components that are the same as the corresponding components of the second embodiment. Such components will not be described in detail.

The body composition measurement device 10 of the second embodiment includes at least two or more simulation resistor units. A body composition measurement device 80 of the third embodiment includes a connection unit that can be connected with the simulation resistor unit instead of the simulation resistor units.

Figure 5:
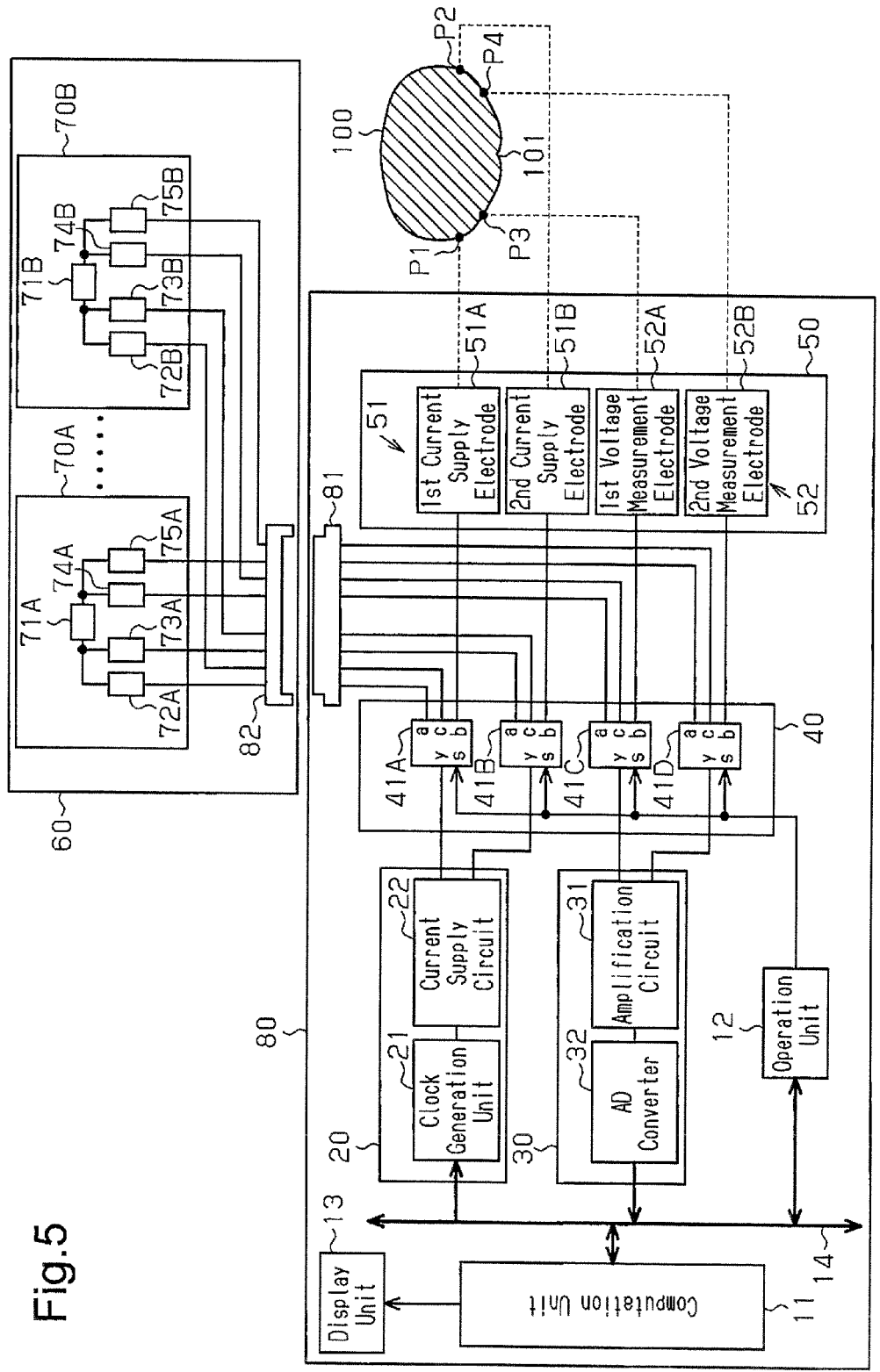
FIG. 5 is a diagram of a body composition measurement device of a third embodiment.

The configuration of the body composition measurement device 80 of the third embodiment will now be described with reference to the block diagram of FIG. 5.

The body composition measurement device 80 includes a connection unit 81 connected to the first terminal (a) and the third terminal (c) of each of the fifth switching circuit 41A, the sixth switching circuit 41B, the seventh switching circuit 41C, and the eighth switching circuit 41D configuring the switching unit 40. The connection unit 81 has, for example, a socket insert unit with a multi-pin socket.

The connection unit 81 can be connected to the correction resistor unit 60. Specifically, the connection unit 81 has a configuration that can be connected with a resistance connection unit 82, which is a socket insert unit with a multi-pin socket, of the correction resistor unit 60. The correction resistor unit 60 includes at least two or more simulation resistor units. The body composition measurement device 80 and the correction resistor unit 60 have the same configuration as the body composition measurement device 10 of the second embodiment shown in FIG. 3 by connecting the connection unit 81 and the resistance connection unit 82. The body composition measurement device 80 can perform the same operation as the body composition measurement device 10 of the second embodiment by connecting the correction resistor unit 60 to the switching unit 40 through the connection unit 81.

To check the characteristic variation and the characteristic fluctuation of the circuit block and the measurement path used in the human body resistance measurement of the measuring subject, the body composition measurement device 80 is connected to the correction resistor unit 60 through the connection unit 81. The body composition measurement device 80 and the correction resistor unit 60 have the configuration of the body composition measurement device 10 of the second embodiment. The body composition measurement device 80 checks the characteristic variation and the characteristic fluctuation of the circuit block and the measurement path used in the human body resistance measurement of the measuring subject by measuring the simulation resistor of the connected correction resistor unit 60. The body composition measurement device 80 can measure the amount of visceral fat of the measuring subject with the configuration from which the correction resistor unit 60 is disconnected. The body composition measurement device 80 reflects the values of the characteristic variation and the characteristic fluctuation of the circuit block and the measurement path on the body composition measurement of the measuring subject using the body composition measurement device 80.

The characteristic variation and the characteristic fluctuation of the circuit block and the measurement path used in the human body resistance measurement of the measuring subject are effective when checked under the following situations, for example. The checking timing is the time of shipping inspection in the manufacturing step of the body composition measurement device 80. Alternatively, the checking timing is the time of usage after a long non-usage period of the body composition measurement device 80. The checking timing may also be when a change occurs in the usage environment condition of the body composition measurement device 80 such as the temperature or the humidity.

Figure 6A:
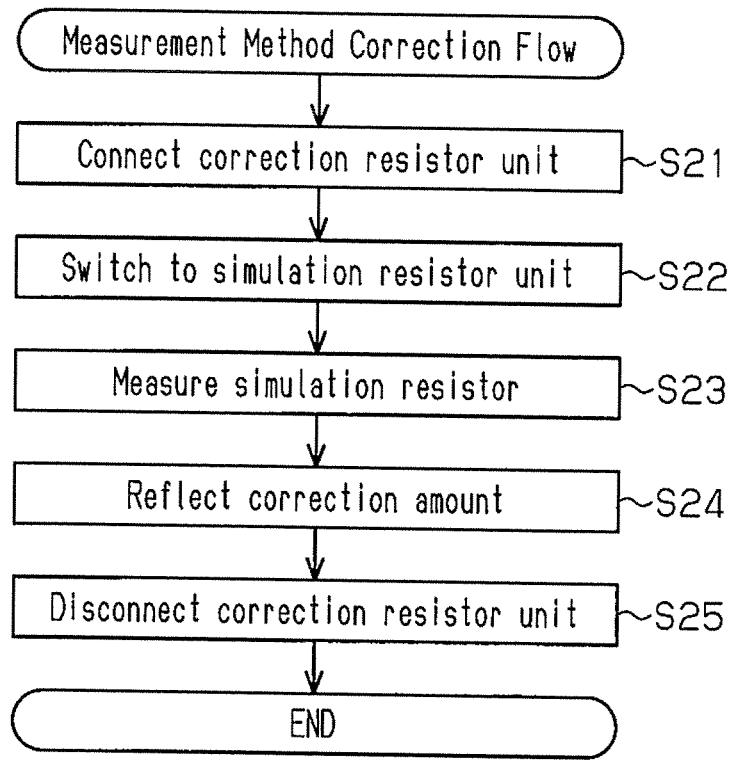
FIG. 6A is a flowchart of a correction process performed on a body composition measurement in the body composition measurement device of the third embodiment.

The flow for correcting the body composition measurement of reflecting the characteristic variation and the characteristic fluctuation of the circuit block and the measurement path used in the human body resistance measurement of the measuring subject on the body composition measurement of the measuring subject with the body composition measurement device 80 will now be described with reference to FIG. 6A.

The computation unit 11 and an operator sequentially execute each of steps S21 to S25 when correcting the body composition measuring method using the body composition measurement device 80 and the correction resistor unit 60.

When correcting the body composition measuring method, the operator connects the correction resistor unit 60 in step S21. In step S22, the operator controls the switching unit 40 through the operation of the operation unit 12. The switching unit 40 selects the correction resistor unit 60. In step S23, the computation unit 11 measures the resistance of the human body simulation resistor 71 of the correction resistor unit 60. In step S24, the computation unit 11 reflects the measurement result of the human body simulation resistor 71 of the correction resistor unit 60 on the body composition measuring method of the measuring subject using the body composition measurement device 80. The user disconnects the correction resistor unit 60 in step S25.

Figure 6B:
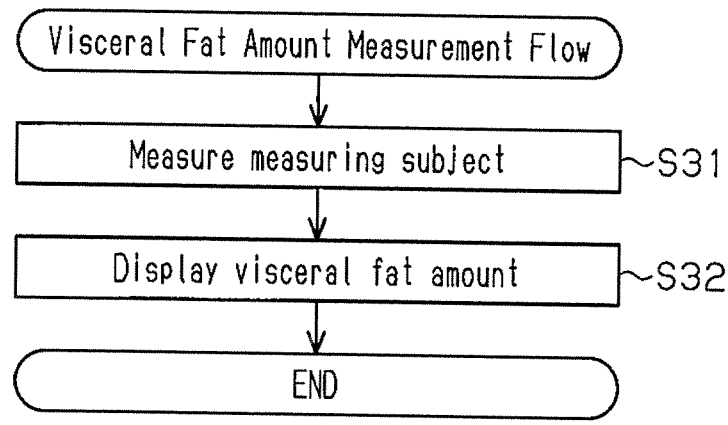
FIG. 6B is a flowchart for measuring the body composition.

The flow for measuring the amount of visceral fat of the measuring subject in which the measurement result of the human body simulation resistor 71 of the correction resistor unit 60 is reflected on the body composition measuring method will now be described with reference to FIG. 6B.

The computation unit 11 and the measuring subject execute steps S31 and S32 when measuring the amount of visceral fat using the body composition measurement device 80.

When measuring the amount of visceral fat, the voltage detection unit 30 detects the voltage generated by the current supplied to the abdomen 100 of the measuring subject in step S31. In step S32, the computation unit 11 estimates the amount of visceral fat based on the body composition measuring method on which the measurement result of the correction resistor unit 60 is reflected, and displays the same on the display unit 13.

The detachable resistance connection unit 82 may be attached to the electrode unit 50.

The body composition measurement device 80 of the present embodiment has advantages (1) to (3) of the body composition measurement device 10 in the first and second embodiments. The body composition measurement device 80 of the present embodiment also has the following advantage.

(4) The body composition measurement device 80 includes the current generation unit 20, the voltage detection unit 30, the computation unit 11, the operation unit 12, the switching unit 40, the electrode unit 50, and the connection unit 81. The connection unit 81 of the body composition measurement device 80 is configured to enable connection to and disconnection from the correction resistor unit 60. According to such configuration, the body composition measurement device 80 measures the resistance of the correction resistor unit 60 using the circuit block and the measurement path used in the human body resistance measurement of the measuring subject by connecting the correction resistor unit 60 to the connection unit 81. Thus, the body composition measurement device 80 is able to check the characteristic variation and the characteristic fluctuation of the circuit block and the measurement path used in the human body resistance measurement of the measuring subject. The body composition measurement device 80 thus reflects the measurement result of the resistance of the correction resistor unit 60 on the body composition measuring method on the body composition measuring method of the measuring subject. Furthermore, the body composition measurement device 80 may measure the amount of visceral fat of the measuring subject with a simple configuration by separating the correction resistor unit 60 from the connection unit 81. Moreover, the body composition measurement device 80 estimates, with high accuracy, the measurement of the amount of visceral fat of the measuring subject with a simple configuration using the body composition measuring method that reflects the measurement result of the resistance of the correction resistor unit 60.

Fourth Embodiment

Compared to the body composition measurement device 10 of the first embodiment, the body composition measurement device 10 of a fourth embodiment differs in the following portions but is otherwise the same. Same reference numerals are given to those components that are the same as the corresponding components of the first embodiment. Such components will not be described in detail.

The body composition measurement device 10 of the first embodiment includes the current supply electrode pair 51 and the voltage measurement electrode pair 52 connected to the second terminal (b) of each of the first switching circuit 40A, the second switching circuit 40B, the third switching circuit 40C, and the fourth switching circuit 40D. The body composition measurement device 10 of the second embodiment includes the current supply electrode pair 51 connected to both of the first switching circuit 40A and the second switching circuit 40B. The current supply electrode pair 51 is connected to the second terminal (b) of the first switching circuit 40A and the first terminal (a) of the second switching circuit 40B.

Figure 7:
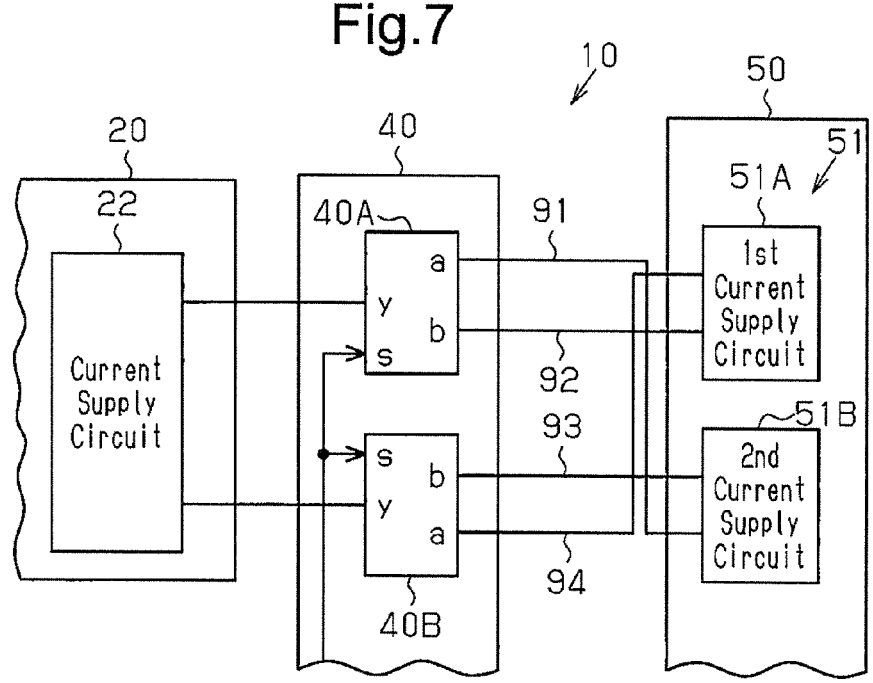
FIG. 7 is a block diagram of a body composition measurement device in a fourth embodiment.

The configuration of the current generation unit 20, the switching unit 40, and the electrode unit 50 in the body composition measurement device 10 of the fourth embodiment will now be described with reference to the block diagram of FIG. 7.

The first switching circuit 40A and the second switching circuit 40B of the switching unit 40 connect the common terminal (y) to the current supply circuit 22 of the current generation unit 20. The current supply electrode pair 51 is connected to each of the first switching circuit 40A and the second switching circuit 40B. The first current supply electrode 51A of the current supply electrode pair 51 is connected to the second terminal (b) of the first switching circuit 40A and the first terminal (a) of the second switching circuit 40B. The second current supply electrode 51B is connected to the first terminal (a) of the first switching circuit 40A and the second terminal (b) of the second switching circuit 40B.

When measuring the human body resistance of the abdomen 100 of the measuring subject using the body composition measurement device 10, the current supply circuit 22 supplies alternating current to the current supply electrode pair 51.

Figure 8:
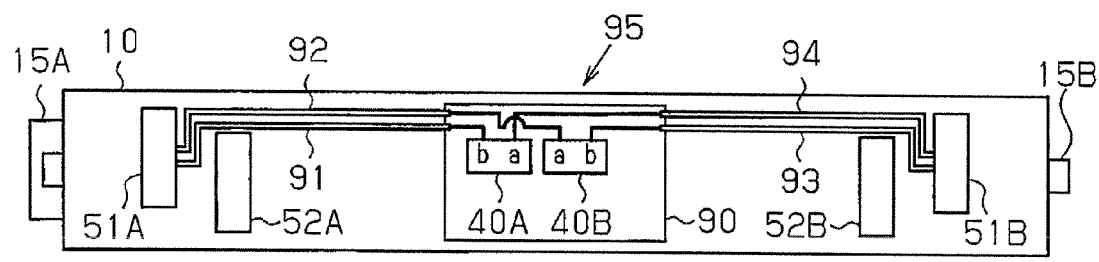
FIG. 8 is a schematic diagram of the body composition measurement device in the fourth embodiment.

The configuration of the body composition measurement device 10 will now be described with reference to the schematic diagram of FIG. 8.

The body composition measurement device 10 is belt-shaped and attached to the abdomen 100 of the measuring subject. The body composition measurement device 10 includes a first fastener 15A and a second fastener 15B. The body composition measurement device 10 is attached to the abdomen 100 of the measuring subject by coupling the first fastener 15A and the second fastener 15B around the abdomen of the measuring subject.

The body composition measurement device 10 includes a circuit substrate 90 with a circuit block including the current generation unit 20, the voltage detection unit 30, the computation unit 11, the operation unit 12, and the switching unit 40. The body composition measurement device 10 includes the first current supply electrode 51A and the second current supply electrode 51B configuring the current supply electrode pair 51, and the first voltage measurement electrode 52A and the second voltage measurement electrode 52B configuring the voltage measurement electrode pair 52. The first current supply electrode 51A is connected to the circuit block mounted on the circuit substrate 90 by a first wiring unit including a first connection cable 91 and a circuit substrate wiring 95, and a second wiring unit including a second connection cable 92 and the circuit substrate wiring 95. The second current supply electrode 51B is connected to the circuit block mounted on the circuit substrate 90 by a third wiring unit including a third connection cable 93 and the circuit substrate wiring 95, and a fourth wiring unit including a fourth connection cable 94 and the circuit substrate wiring 95.

The current supply electrode pair 51 and the voltage measurement electrode pair 52 contact the body composition measuring portion of the measuring subject when the body composition measurement device 10 is attached to the abdomen 100 of the measuring subject. When measuring the amount of visceral fat of the measuring subject using the body composition measurement device 10, the alternating current supplied by the current supply circuit 22 is supplied to the first current supply electrode 51A and the second current supply electrode 51B through the first switching circuit 40A and the second switching circuit 40B. If there is a difference in the characteristic impedance between the connection path of the first switching circuit 40A and the first current supply electrode 51A and the connection path of the second switching circuit 40B and the second current supply electrode 51B, an error may occur in the human body resistance measurement value of the measuring subject due to the difference in the voltage drop at the connection path.

The first switching circuit 40A and the second switching circuit 40B of the body composition measurement device 10 are connected to both of the first current supply electrode 51A and the second current supply electrode 51B by the first wiring unit and the second wiring unit and by the third wiring unit and the fourth wiring unit. When measuring the amount of visceral fat of the measuring subject using the body composition measurement device 10, the first switching circuit 40A and the second switching circuit 40B selectively switch the first switching circuit 40A and the second switching circuit 40B at a predetermined period under the control of the computation unit 11. That is, the body composition measurement device 10 switches the first wiring unit and the second wiring unit and switches the third wiring unit and the fourth wiring unit at a predetermined period as a path of the current supplied to the current supply electrode pair 51. The first wiring unit and the second wiring unit have substantially the same wiring length, are substantially the same wiring path, and are substantially symmetric. The third wiring unit and the fourth wiring unit have substantially the same wiring length, are substantially the same wiring path, and are substantially symmetric.

A connection relationship of the third switching circuit 40C and the fourth switching circuit 40D with the first voltage measurement electrode 52A and the second voltage measurement electrode 52B is similar to that of the first switching circuit 40A and the second switching circuit 40B with the first current supply electrode 51A and the second current supply electrode 51B.

The body composition measurement device 10 of the present embodiment has advantages (1) to (3) of the body composition measurement device 10 of the first and second embodiments. The body composition measurement device 10 of the present embodiment also has the following advantages.

(5) In the body composition measurement device 10, the switching unit 40 includes the first switching circuit 40A and the second switching circuit 40B. The body composition measurement device 10 includes the first current supply electrode 51A and the second current supply electrode 51B. The first switching circuit 40A and the second switching circuit 40B are connected to both of the first current supply electrode 51A and the second current supply electrode 51B by the first wiring unit and the fourth wiring unit and by the second wiring unit and the third wiring unit. When measuring the amount of visceral fat of the measuring subject using the body composition measurement device 10, the first switching circuit 40A and the second switching circuit 40B selectively switch the first switching circuit 40A and the second switching circuit 40B at a predetermined period under the control of the computation unit 11. According to such configuration, the body composition measurement device 10 switches the first wiring unit and the third wiring unit and switches the second wiring unit and the fourth wiring unit at a predetermined period as a path of the current supplied to the first current supply electrode 51A and the second current supply electrode 51B. Thus, the body composition measurement device 10 matches the characteristic impedance of the connection path of the first switching circuit 40A and the first current supply electrode 51A with the connection path of the second switching circuit 40B and the second current supply electrode 51B. The body composition measurement device 10 is thus able to measure the human body resistance of the measuring subject with high accuracy.

(6) In the body composition measurement device 10, the first switching circuit 40A is connected to the first current supply electrode 51A and the second current supply electrode 51B by the first wiring unit including the first connection cable 91 and the circuit substrate wiring 95 and the fourth wiring unit including the fourth connection cable 94 and the circuit substrate wiring 95. In the body composition measurement device 10, the second switching circuit 40B is connected to the first current supply electrode 51A and the second current supply electrode 51B by the second wiring unit including the second connection cable 92 and the circuit substrate wiring 95 and the third wiring unit including the third connection cable 93 and the circuit substrate wiring 95. The first wiring unit and the second wiring unit in addition to the third wiring unit and the fourth wiring unit have substantially the same wiring length, are substantially the same wiring path, and are substantially symmetric. When measuring the amount of visceral fat of the measuring subject using the body composition measurement device 10, the first switching circuit 40A and the second switching circuit 40B selectively switch the first switching circuit 40A and the second switching circuit 40B at a predetermined period under the control of the computation unit 11. According to such configuration, the body composition measurement device 10 switches the first wiring unit and the third wiring unit and switches the second wiring unit and the fourth wiring unit at a predetermined period as a path of the current supplied to the first current supply electrode 51A and the second current supply electrode 51B. Thus, when the characteristic impedances of the first wiring unit to the fourth wiring unit fluctuate, the body composition measurement device 10 cancels such fluctuation and measures the amount of visceral fat of the measuring subject. This allows the body composition measurement device 10 to measure the human body resistance of the measuring subject with higher accuracy.

Fifth Embodiment

Compared to the body composition measurement device 10 of the first and second embodiments, the body composition measurement device 10 of a fifth embodiment differs in the following portions but is otherwise the same. Same reference numerals are given to those components that are the same as the corresponding components of the first second embodiment. Such components will not be described in detail.

The body composition measurement device 10 of the first and second embodiments includes the current supply electrode pair 51 and the voltage measurement electrode pair 52. The body composition measurement device 10 of the fifth embodiment includes a plurality of disconnected regions in which the current supply electrode pair 51 and the voltage measurement electrode pair 52 are electrically disconnected.

Figure 9B:
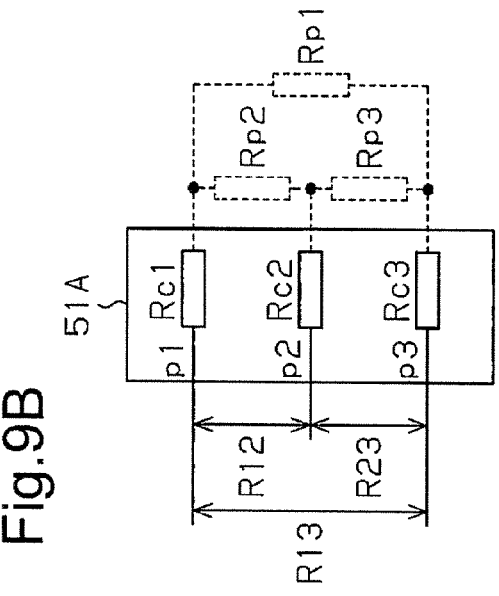
FIG. 9B is an equivalent circuit diagram of an electrode unit.
Figure 9A:
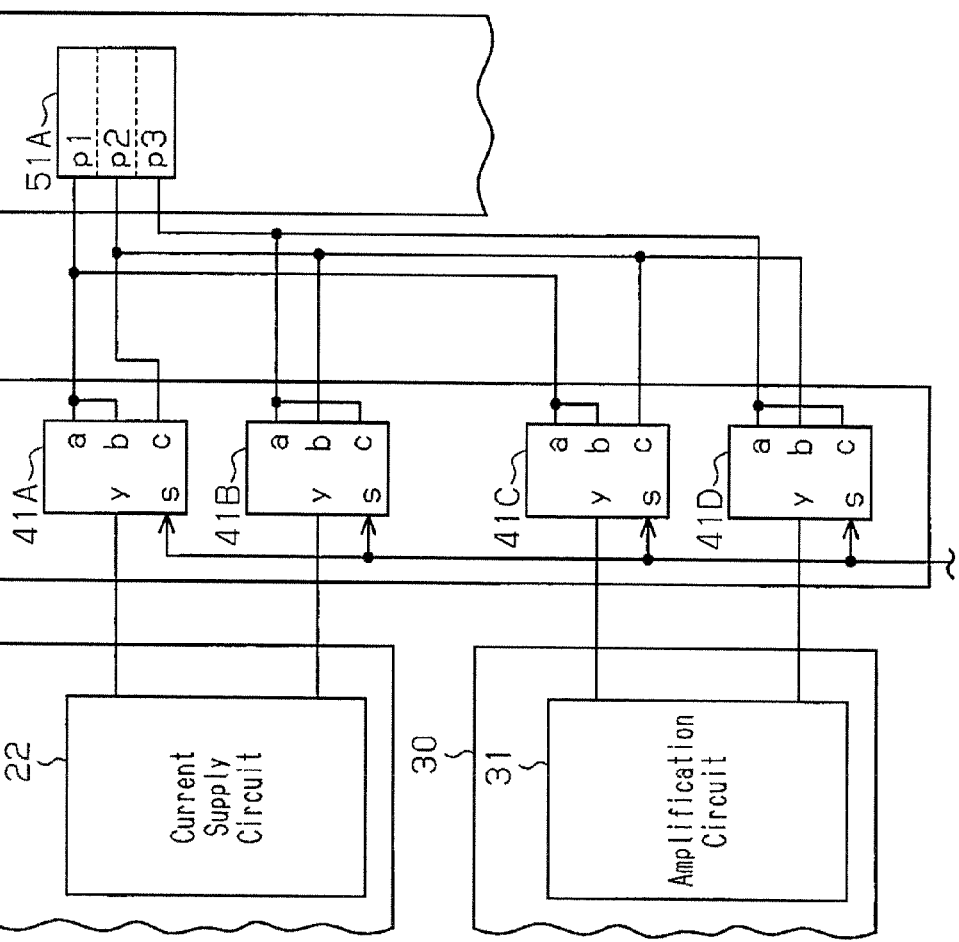
FIG. 9A is a block diagram of the body composition measurement device in the fourth embodiment.

The configuration of the current generation unit 20, the voltage detection unit 30, the switching unit 40, and the electrode unit 50 in the body composition measurement device 10 of the fifth embodiment will now be described with reference to the block diagram of FIG. 9A.

The switching unit 40 of the body composition measurement device 10 includes the fifth switching circuit 41A, the sixth switching circuit 41B, the seventh switching circuit 41C, and the eighth switching circuit 41D. The electrode unit 50 includes the first current supply electrode 51A.

The fifth switching circuit 41A, the sixth switching circuit 41B, the seventh switching circuit 41C, and the eighth switching circuit 41D of the switching unit 40 connect the common terminal (y) connected to any one of the first terminal (a), the second terminal (b), and the third terminal (c) according to a control signal input to the control terminal (s). The first current supply electrode 51A includes a first region (a), a second region (b), and a third region (c) as electrically disconnected regions. When the first current supply electrode 51A contacts the measuring subject, the first current supply electrode 51A and the human body resistance of the measuring subject configure the equivalent circuit shown in FIG. 9B. In FIG. 9B, (Rc1), (Rc2), and (Rc3) indicate the contact resistance of the first region (a), the second region (b), and the third region (c) of the first current supply electrode 51A and the measuring subject. In FIG. 9B, (Rp1) indicates the human body resistance of the measuring subject positioned between the first region (a) and the third region (c) of the first current supply electrode 51A. In FIG. 9B, (Rp2) indicates the human body resistance of the measuring subject positioned between the first region (a) and the second region (b) of the first current supply electrode 51A. In FIG. 9B, (Rp3) in FIG. 9B indicates the human body resistance of the measuring subject positioned between the second region (b) and the third region (c) of the first current supply electrode 51A.

A resistance (R12) between the first region (a) and the second region (b) of the first current supply electrode 51A, a resistance (R23) between the second region (b) and the third region (c), and a resistance (R13) between the first region (a) and the third region (c) are values expressed with the following equations (1) to (3). Therefore, the contact resistance (Rc2) can be obtained by measuring the resistances (R12), (R23), and (R13), as shown with equation (4).

$$R12 = Rc1 + Rc2 + Rp2 \quad (1)$$

$$R23 = Rc2 + Rc3 + Rp3 \quad (2)$$

$$R13 = Rc1 + Rc3 + Rp1 = Rc1 + Rc3 + Rp2 + Rp3 \quad (3)$$

$$Rc2 = (R12 + R23 - R13)/2 \quad (4)$$

The body composition measurement device 10 can measure the resistances (R12), (R23), and (R13) shown in FIG. 9B by switching the fifth switching circuit 41A, the sixth switching circuit 41B, the seventh switching circuit 41C, and the eighth switching circuit 41D.

When measuring the resistance (R12), the fifth switching circuit 41A, the sixth switching circuit 41B, the seventh switching circuit 41C, and the eighth switching circuit 41D select the second terminal (b) according to the control signal from the operation unit 12. The supply current from the current supply circuit 22 is supplied to the first region (a) and the second region (b) of the first current supply electrode 51A through the fifth switching circuit 41A and the sixth switching circuit 41B. The voltage generated in the first region (a) and the second region (b) of the first current supply electrode 51A is supplied to the amplification circuit 31 through the seventh switching circuit 41C and the eighth switching circuit 41D. The computation unit 11 determines the resistance based on the output of the amplification circuit 31. The computation unit 11 can determine the resistance (R23) and the resistance (R13) through a similar procedure.

The body composition measurement device 10 can obtain the contact resistance in the second current supply electrode 51B in the same manner as the first voltage measurement electrode 52A. The body composition measurement device 10 divides the second current supply electrode 51B to the first region (a), the second region (b), and the third region (c), which are electrically disconnected. The body composition measurement device 10 obtains the contact resistance assuming the connection of the second current supply electrode 51B and the switching unit 40 is similar to the connection of the first current supply electrode 51A and the switching unit 40. In the first voltage measurement electrode 52A and the second voltage measurement electrode 52B, the body composition measurement device 10 can also obtain the contact resistance with a similar divided configuration and a similar connection to the switching unit 40.

The body composition measurement device 10 of the present embodiment has advantages (1) to (3) of the body composition measurement device 10 of the first and second embodiments. The body composition measurement device 10 of the present embodiment also has the following advantage.

(7) The current supply electrode pair 51 and the voltage measurement electrode pair 52 of the body composition measurement device 10 include the first region (a), the second region (b), and the third region (c) as electrically disconnected regions. The fifth switching circuit 41A, the sixth switching circuit 41B, the seventh switching circuit 41C, and the eighth switching circuit 41D of the switching unit 40 connect the common terminal (y) to any one of the first terminal (a), the second terminal (b), and the third terminal (c) according to the control signal input to the control terminal (s). According to such configuration, the body composition measurement device 10 measures the resistance between the divided regions that are electrically disconnected. Thus, the computation unit 11 obtains the contact resistance of the current supply electrode pair 51 and the voltage measurement electrode pair 52. The body composition measurement device 10 issues a warning to the user when the contact resistance obtained by the computation unit 11 indicates a value outside the assumed range. The user is thus able to recognize that the measurement state is abnormal.

Other Embodiments

The present invention includes embodiments other than the first to fifth embodiments. Modifications of the first to fifth embodiments serving as other embodiments of the present invention will now be described below. The modifications may be combined with each other.

In the body composition measurement device 10 of the first and second embodiments, the switching unit 40 includes a switching circuit. The configuration of the switching unit 40 is not limited to the configuration of the first and second embodiments. For example, in the body composition measurement device 10 of a modification, the switching unit 40 includes a multiplexer. Alternatively, the switching unit 40 includes an analog switch. The switching unit 40 thus merely needs to have a configuration in which the connection relationship can be changed according to the control signal.

In the body composition measurement device 10 of the first and second embodiments, the operation unit 12 includes a plurality of operation switches. The configuration of the operation unit 12 is not limited to the configuration shown in the first and second embodiments. For example, in the body composition measurement device 10 of a modification, the operation unit 12 is configured by a sequencer that performs automatic control.

The body composition measurement device 10 of the first and second embodiments measures the human body resistance of the abdomen 100 of the measuring subject by holding the current supply electrode pair 51 and the voltage measurement electrode pair 52 in contact with the periphery of the abdomen 100 of the measuring subject. However, the contacting area of the current supply electrode pair 51 and the voltage measurement electrode pair 52 is not limited to the area shown in the first and second embodiments. For example, the body composition measurement device 10 of a modification has electrodes forming the current supply electrode pair 51 and the voltage measurement electrode pair 52 that the body trunk of the measuring subject spaced apart by a predetermined amount or greater. The body composition measurement device 10 measures the subcutaneous fat of the measuring subject.

The body composition measurement device 80 of the third embodiment includes the connection unit 81, which is a socket insert unit with a multi-pin socket, as the connection unit, and is connectable with the correction resistor unit 60 including the resistance connection unit 82, which is a socket insert unit with a multi-pin socket. However, the connection unit is not limited to the configuration shown in the third embodiment. For example, the body composition measurement device 10 of a modification includes a connecting region formed as part of a wiring pattern of a circuit substrate with a circuit block arranged in the body composition measurement device 80 as the connection unit. The body composition measurement device 80 can be connected to the correction resistor unit 60 by pushing a resistor to contact the connecting region.

In the body composition measurement device 10 of the second embodiment, the correction resistor unit 60 includes the second simulation resistor unit 70A, the third simulation resistor unit 70B, and the fourth simulation resistor unit 70C. However, the configuration of the correction resistor unit 60 is not limited to the configuration shown in the second embodiment. For example, in the body composition measurement device 10 of a modification, the correction resistor unit 60 includes four types of simulation resistor units. Alternatively, the correction resistor unit 60 may include four or more types of simulation resistor units.

In the body composition measurement device 10 and the body composition measurement device 80 of the first to fifth embodiments, the electrode unit 50 includes the current supply electrode pair 51 and the voltage measurement electrode pair 52. The configuration of the electrode unit 50 is not limited to the area shown in the first to fifth embodiments. For example, the body composition measurement device 10 of a modification includes a current supply adhesive pad pair, in which an adhesive gel is applied to the surface, and the voltage measurement electrode pair. Alternatively, the body composition measurement device 10 of a modification includes the current supply adhesive pad pair and the voltage measurement adhesive pad pair.

APPENDIX RELATED TO MEANS FOR SOLVING THE PROBLEMS

The means for solving the problems may be as each supplemental means described below.

(1) Supplemental means 1 includes "the body composition measurement device according to claim 5, wherein the simulation resistor unit connects the first and third electrode contact simulation resistors and the second electrode and fourth electrode contact simulation resistors to both ends of the human body simulation resistor."

(2) Supplemental means 2 includes "the body composition measurement device according to claim 5, wherein the computation unit outputs the body composition related information based on an approximate curve and a voltage that is generated at the voltage measurement electrode pair and detected by the voltage detection unit."

DESCRIPTION OF REFERENCE CHARACTERS 10 body composition measurement device
11 computation unit
12 operation unit
20 current generation unit
30 voltage detection unit
40 switching unit
40A first switching circuit
40B second switching circuit
51 current supply electrode pair
51A first current supply electrode
51B second current supply electrode
52 voltage measurement electrode pair
60 correction resistor unit
70 dummy resistor unit
71 human body simulation resistor
72 first electrode contact simulation resistor
73 third electrode contact simulation resistor
74 fourth electrode contact simulation resistor
75 second electrode contact simulation resistor
80 body composition measurement device
81 connection unit
100 abdomen

The invention claimed is:

1. A body composition measurement device comprising:
a current supply electrode pair and a voltage measurement electrode pair that contact an abdomen of a measuring subject;
a current generation unit configured to generate current;
a voltage detection unit configured to detect voltage generated by a correction resistor unit to measure resistance of the correction resistor unit, wherein the voltage detection unit is configured to detect voltage generated by the voltage measurement electrode pair using current generated by the current generation unit and supplied to the abdomen of the measuring subject through the current supply electrode pair; and
a computation unit configured to generate body composition related information based on the voltage generated by the voltage measurement electrode pair and the voltage generated by the correction resistor unit, which are detected by the voltage detection unit, wherein the correction resistor unit includes a plurality of simulation resistor units, and each of the plurality of simulation resistor units includes a human body simulation resistor configured to simulate an abdomen of a measuring subject, and wherein the computation unit is configured to derive an approximate curve using measurement values of the plurality of human body simulation resistors of the plurality of simulation resistor units and generate the body composition related information using the approximate curve.

2. The body composition measurement device according to claim 1, wherein the computation unit configured to generate visceral fat amount related information as the body composition related information.

3. The body composition measurement device according to claim 1, comprising:

an operation unit configured to generate a control signal; and a switching unit configured to supply either one of the current supply electrode pair and the correction resistor unit with the current generated by the current generation unit in accordance with the control signal generated by the operation unit, wherein the switching unit is configured to select the voltage of either one of the voltage measurement electrode pair and the correction resistor unit and supplies the voltage to the voltage detection unit in accordance with the control signal.

4. The body composition measurement device according to claim 1, wherein each of the plurality of simulation resistor units includes:

a first electrode contact simulation resistor and a second electrode contact simulation resistor configured to simulate contact of the current supply electrode pair and the abdomen of the measuring subject, and a third electrode contact simulation resistor and a fourth electrode contact simulation resistor configured to simulate contact of the voltage measurement electrode pair and the abdomen of the measuring subject.

5. The body composition measurement device according to claim 3, wherein the switching unit includes a first switching circuit and a second switching circuit;

the current supply electrode pair includes a first current supply electrode and a second current supply electrode;

each of the first switching circuit and the second switching circuit includes a common terminal, into which the current generated by the current generation unit is input, and a first terminal and a second terminal, from which the current generated by the current generation unit is output;

the first terminal of the first switching circuit is connected to the first current supply electrode by a first wiring unit;

the second terminal of the first switching circuit is connected to the second current supply electrode by a second wiring unit;

the first terminal of the second switching circuit is connected to the second current supply electrode by a third wiring unit;

the second terminal of the second switching circuit is connected to the first current supply electrode by a fourth wiring unit;

the first wiring unit and the fourth wiring unit are arranged to form a substantially symmetrical geometric shape, and the second wiring unit and the third wiring unit are arranged to form a substantially symmetrical geometric shape; and the first switching circuit and the second switching circuit are configured to alternately output the current generated by the current generation unit from the first terminal and the second terminal.

6. The body composition measurement device according to claim 3, wherein each of the current supply electrode pair and the voltage measurement electrode pair includes a plurality of disconnected regions that are electrically disconnected;

the switching unit is configured to supply one of the plurality of disconnected regions with the current generated by the current generation unit in accordance with the control signal generated by the operation unit; and the switching unit is configured to select a voltage of one of the plurality of disconnected regions and supplies the voltage to the voltage detection unit in accordance with the control signal generated by the operation unit.

* * * * *